United States Patent
Hutchinson

(10) Patent No.: US 10,107,883 B2
(45) Date of Patent: Oct. 23, 2018

(54) ULTRAFAST MRI SYSTEM AND METHOD

(71) Applicant: Michael Hutchinson, New York, NY (US)

(72) Inventor: Michael Hutchinson, New York, NY (US)

(*) Notice: Subject to any disclaimer, the term of this patent is extended or adjusted under 35 U.S.C. 154(b) by 845 days.

(21) Appl. No.: 14/671,528

(22) Filed: Mar. 27, 2015

(65) Prior Publication Data
US 2016/0282429 A1    Sep. 29, 2016

(51) Int. Cl.
*G01R 33/561* (2006.01)
*G01R 33/565* (2006.01)
*G01R 33/50* (2006.01)
*G01R 33/387* (2006.01)
*G01R 33/32* (2006.01)
(Continued)

(52) U.S. Cl.
CPC ...... *G01R 33/5611* (2013.01); *G01R 33/3415* (2013.01); *A61B 5/055* (2013.01); *G01R 33/483* (2013.01); *G01R 33/561* (2013.01)

(58) Field of Classification Search
CPC ............... G01R 33/00; G01R 33/0017; G01R 33/0023; G01R 33/20; G01R 33/28; G01R 33/3415; G01R 33/38; G01R 33/387; G01R 33/3875; G01R 33/44; G01R 33/46; G01R 33/4608; G01R 33/4633; G01R 33/48; G01R 33/482; G01R 33/4822; G01R 33/4824; G01R 33/4826; G01R 33/483; G01R 33/4833; G01R 33/4835; G01R 33/54; G01R 33/543; G01R 33/56; G01R 33/561; G01R 33/5611; G01R 33/565;
(Continued)

(56) References Cited

U.S. PATENT DOCUMENTS 6,771,071 B1    8/2004    Wright
8,368,397 B2*   2/2013    Sakakura ............... A61B 5/055
                                                  324/307
(Continued)

OTHER PUBLICATIONS

Lauterbur PC, Image formation by induced local interactions. Nature 1973; 242(1):190.
(Continued)

*Primary Examiner* — Hoai-An D Nguyen
(74) *Attorney, Agent, or Firm* — Cooper & Dunham LLP

(57) ABSTRACT

Magnetic Resonance Imaging (MRI), which is given the acronym ULTRA (Unlimited Trains of Radio Acquisitions), can eliminate magnetic gradient reversals and allow simultaneous MR signal acquisition from the entire object volume in each of a multitude of very small receiver coils arranged in a 3D array around the imaging volume. This permits a rate of MR signal acquisition that is greatly increased (e.g. 256 times) compared with existing techniques, with a full 3D image constructed in as little as 1 millisecond. Furthermore, noise—both audible and electrical—is substantially reduced. The advantages over conventional MRI include:

1. Clinical imaging can be completed in seconds, with good signal-to-noise ratio;
2. Signal-to-noise ratio is further increased by eliminating RF noise due to gradient switching;
3. Real-time functional MRI is possible, on millisecond timescales;
4. With single breath holds, high quality imaging of thorax and abdomen is possible.
5. ULTRA greatly reduces audible noise and vibration.

25 Claims, 3 Drawing Sheets

(51) Int. Cl.
*G01R 33/3415* (2006.01)
*A61B 5/055* (2006.01)
*G01R 33/483* (2006.01)

(58) Field of Classification Search
CPC .......... G01R 33/56554; G01R 33/5659; A61B 5/00; A61B 5/05; A61B 5/055
USPC ........................................ 324/300, 307, 309
See application file for complete search history.

(56) References Cited

U.S. PATENT DOCUMENTS

| | | | | |
|---|---|---|---|---|
| 9,097,777 | B2* | 8/2015 | Weber | G01R 33/4833 |
| 9,784,814 | B2* | 10/2017 | Tsai | G01R 35/005 |
| 2007/0170920 | A1* | 7/2007 | Hanawa | G01R 33/56375 |
| | | | | 324/318 |
| 2012/0301000 | A1* | 11/2012 | Bornert | G01N 24/082 |
| | | | | 382/130 |
| 2014/0347049 | A1* | 11/2014 | Tsai | G01R 35/005 |
| | | | | 324/307 |
| 2017/0003364 | A1* | 1/2017 | Harvey | G01R 33/4816 |

OTHER PUBLICATIONS

Mansfield P, Pykett IL, Biological and medical imaging by NMR. J. Mag. Res. 1983; 29(2):355-373.
Hutchinson M, Raff U, Subsecond Data Acquisition Using Multiple Detectors Proceedings, Society for Magnetic Resonance in Medicine, 6th Annual Meeting, New York, 1987; Supplement S1: 459.
Hutchinson M, Raff U, Fast MRI Data Acquisition Using Multiple Detectors. Mag. Res. Med. 1988; 6:87-91.
Kelton JR, Magin RL and Wright SM, An algorithm for rapid image acquisition using multiple receiver coils. Proceedings of the SMRM 8th Annual Meeting (1989) p. 1172.
Ra JB, Rim CY. Fast imaging using subencoding data for multiple detectors. 1993; Mag. Res. Med. 30(1); 142-145.
Roemer PB, Edelstein WA, Hayes CE, Souza SP, Mueller OM, The NMR phased array. Mag. Res. Med. 1990; 16:192-225.
Ocali O, Atalar E, Ultimate Intrinsic Signal-to-Noise Ration in MRI. Mag. Res. Med. 1998;39:462-473.
Sodickson DK, Manning WJ, Simultaneous acquisition of spatial harmonics (SMASH): Fast imaging with radiofrequency coils. Mag. Res. Med. 1997; 38(4):591-603.
Pruessman KP, Weiger M, Scheidegger MB, BoesigerP, SENSE: Sensitivity encoding for fast MRI. Mag. Res. Med. 1999; 42(15):952-962.
Ohliger MA, Grant AK, Sodickson DK, Ultimate intrinsic signal-to-noise ratio for parallel MRI: Electromagnetic field considerations. 2003. Mag.Res. Med. 2003; 50:1018-1030.
Wiesiger F, Boesiger P, Pruessman K, Electrodynamics and ultimate SNR in parallel MR imaging. Mag. Res. Med. 2004; 52:376-390.
Keil B, Wald LL, Massively parallel MRI detector arrays. J. Mag. Res. 2013; 229:75-89.
McDougall MP, Wright SM, 64 channel array coil for single echo acquisition. Mag. Res. Med. 2005; 54:386-392.
Halpren-Manners NW, Kennedy DJ, Trease DR, Teisseyre TZ, Malecek NS, Pines A, Bajaj VS, Gradient-free microfluidic flow labeling using thin magnetic films and remotely detected MRI, J. Mag. Res. 2459 (2014) 135-140.
Sharp JC, King SB, MRI Using Radiofrequency Magnetic Field Phase Gradients, Mag. Res. Med. 63:151-161 (2010).
Yepes-Calderon F, Velasquez A, Lepore N, Beuf O, Magnetic Resonance Image Enhancement by Reducing Receptors' Effective Size and Enabling Multiple Channel Acquisition, 978-1-4244-7929~0/14 2014 IEEE (2014) 2420-2423.
Hutchinson M, Raff U, Is the Fastest MRI a Hologram?,J Neuroimaging 2014; 24; 537-542 (vol. 24 No. 6 Nov./Dec. 2014).

* cited by examiner

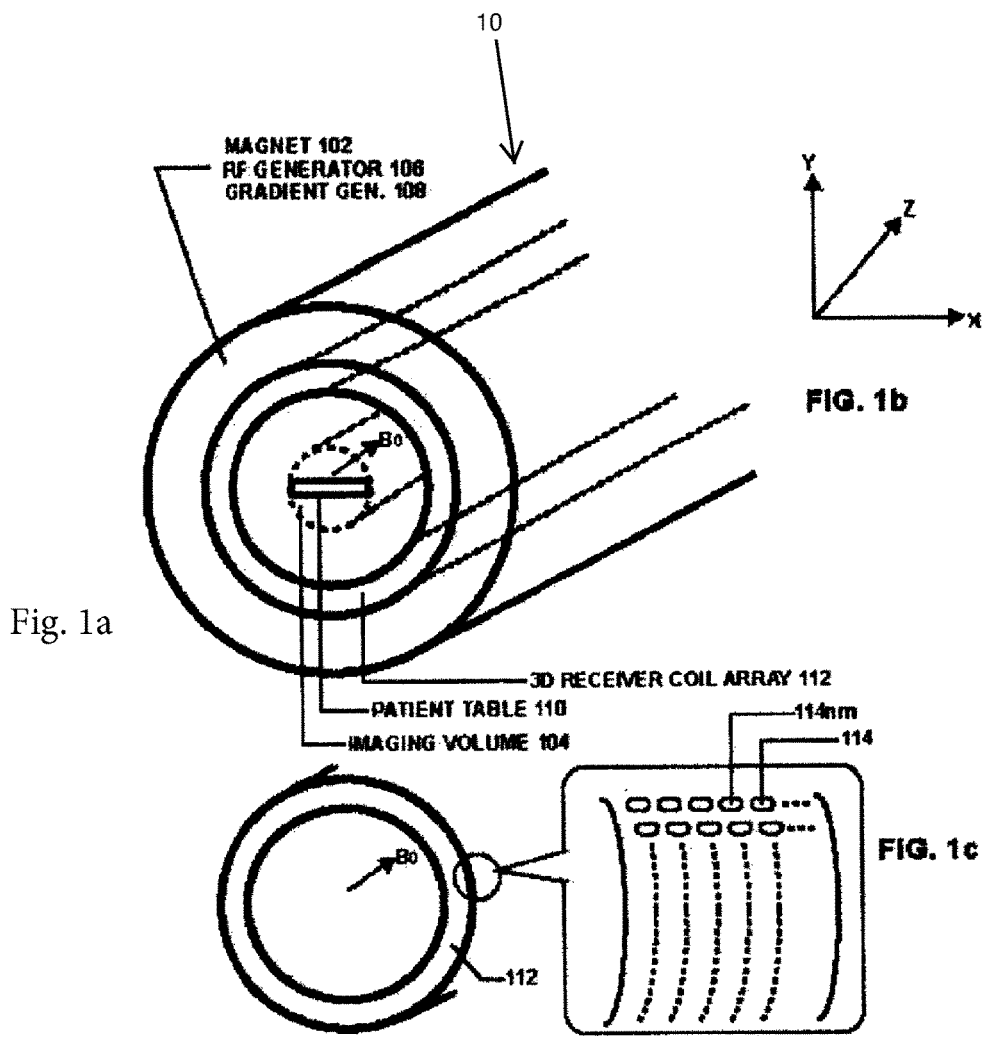
Fig. 1a
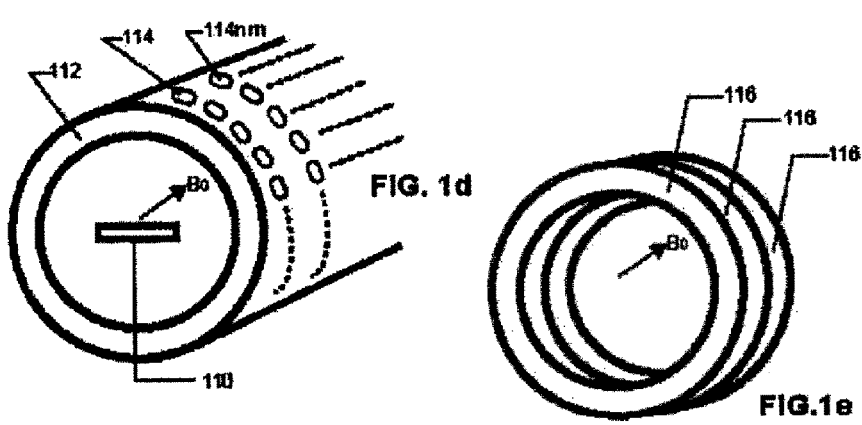

ULTRAFAST MRI SYSTEM AND METHOD

FIELD

This patent specification is in the field of imaging, such as medical imaging, and more specifically relates to rapid three-dimensional (3D) magnetic resonance imaging (MRI).

BACKGROUND

Several references are identified by numerals in parenthesis in this patent specification, and are hereby incorporated by reference. The full citations are listed at the end of the specification. Reference [18] is a paper by the inventor and a person working under his direction regarding the subject matter of the paper.

Real-time MR imaging could exert a profound influence on neuroscience in the future by enabling the direct visualization of neuronal interactions. At this time, however, the known practical embodiments of MRI require at least some degree of gradient encoding, and this in turn sets a lower limit of about 100 ms for volume acquisition.

In the original formulation of MRI by Lauterbur [1], spatial encoding is achieved by applying successive magnetic field gradients to the imaging volume. Each new gradient is associated with a different radiofrequency (RF) excitation, and RF-induced echoes form a line in k-space, discretized into N elements, where N is the dimension of the image matrix. After N progressively increasing gradients, and N echoes, there are N lines in k-space, and the N×N k-space matrix is subjected to a 2-D Fourier transform, rendering the N×N image matrix. In echoplanar imaging (EPI) Mansfield [2] showed that spatial encoding could be achieved by means of trains of gradient reversals after a single RF excitation. An advantage of using gradient reversals is speed; a disadvantage is sensitivity to susceptibility changes and magnetic field inhomogeneities.

More recently studied parallel MRI (pMRI) uses the spatial sensitivities of multiple receiver coils (detectors) arranged around the object for spatial encoding of voxels in a single slice, thus reducing the need for gradient reversals and RF pulses [3, 4]. pMRI images are discussed by Kelton, Magin and Wright [5], and by Ra and Rim [6]. pMRI modifies the Lauterbur-Mansfield approach to include multiple receiver coils, so that if the number of coils is n, then the number of gradient reversals is a factor n times smaller. According to such studies of pMRI, many of the conventional 180° RF pulses can be replaced by short trains of gradient reversals, with an acceptable change in image quality. Thus, pMRI can embrace some of the advantages of EPI, without some of the disadvantages. Because gradient switching is generally several times faster than RF excitations, image quality can be adequately maintained while speed is increased somewhat.

The pMRI initially proposed by Hutchinson [3,4] is for single shot imaging that ignores sources of noise in the surface coils. Subsequent analyses of detector arrays by Roemer [7] and Ocali [8] account to some extent for the effects of noise, with algorithms for conventional gradient encoding. A concept of "ultimate signal-to-noise," [8] can be considered, by which was meant that, at least for gradient encoding, large numbers of small receiver coils—when properly configured—can be more efficient than a single receiver. Sodickson [9], with SMASH, and Pruessmann [10], with SENSE, proposed merging gradient-encoding and spatial sensitivity encoding. These merging techniques can be designated "hybrid" since they use both methods of encoding.

Merging of the two fundamental ways of encoding comes at a considerable price, because for the hybrid techniques ultimate signal-to-noise is reached not with large numbers of coils, but with small numbers (typically 4). Signal-to-noise (SNR) in hybrid pMRI is reduced by 3 sources: (i) electrical noise, (ii) reduced numbers of echoes, and (iii) a critical geometric factor, g, as discussed by Ohliger [11] and Wiesiger [12]. Sources of electrical noise include preamplifiers, coupling between adjacent coils, and body thermal noise. In addition, there is noise from the eddy currents in the body surface due not only to the gradient reversals but also to re-radiation of signal by the coil, which is both a receiver and a dipole radiator. These sources of noise can be reduced, however, and for conventional gradient encoding multiple small coils have been shown to be more efficient than one large coil [7,8] so there is no insurmountable noise problem inherent to small coils. When multiple coils are used to encode, however, there can be an additional problem due to the inefficiency of spatial sensitivity encoding, compared with gradient encoding, when the coils are large. This in turn is due to the slow spatial variations of the spatial sensitivity of each coil. In addition, since there are fewer phase-encoding steps SNR is further reduced. The signal-to-noise ratio is now given by [11,12]:

$$SNR = SNR_{Full}/(\sqrt{R})g \quad (1)$$

where $SNR_{Full}$ is the SNR for gradient-only encoding, R is the acceleration factor (in this case the number of detectors) and g is the geometric factor. The loss factor $\sqrt{R}$ represents the reduced SNR due to the reduced number of phase encoding steps, and could not be mitigated absent phase encoding. The g-factor is intrinsic to the geometry of the coil array, and is a measure of the capacity of the array to compensate for reductions in gradient encoding. For very small numbers of detectors g is close to 1, but as the number of coils increases, and the number of phase-encoding steps correspondingly decreases, g suddenly becomes large and the images are degraded.

It has generally been accepted that for practical purposes this single limitation means that for hybrid techniques acceleration factors need to be at most about 4, so that the rate of acquisition of SNR is about double that of non-parallel techniques. The reason g>1 with increasing accelerations is that the transformations used to obtain the image in conventional pMRI are non-unitary, and the reason for this is that the solutions to Maxwell's equations are "smooth," by which is meant that for large detectors the spatial dependence of the radio field is not as granular as the spatial dependence of the gradients used for conventional encoding. This in turn means that large groups of adjacent pixels may have similar spatial sensitivity profiles.

As R increases, and the number of gradient-encoding steps correspondingly decreases, more and more of the burden of encoding is shouldered by the receiver array. For R=N=4, only 25% of the encoding is gradient-based. With more detectors there is an unsupportable reliance on spatial sensitivity encoding and this leads to rapid image degradation when R>4. The spatial sensitivity maps can be modeled for illustrative purposes by taking, as an approximation to the solutions of Maxwell's equations, only the $1/r^3$ dependence of the near field dipole. This view of an inherent limitation of all constructions of parallel MRI has been challenged by Keil and Wald [13], with a theoretical evaluation suggesting that the spatial sensitivity of small coils could contribute more in spatial encoding in hybrid pMRI while still using some gradient encoding. The original concept for single shot, single slice imaging free of gradient reversals [3,4] was tested several years ago by McDougall and Wright [14], using a 64 channel coil with an acceleration factor of 64. However, this was not for volume encoding but only for a single slice. Proposals have been published to employ static magnetic field gradients produced by thin magnetic films to encode flow [15], to use two or three RF phase gradients in an arrangement free of magnetic gradients [16], and to use a flexible array coils populated with multiple coils in multi-slice-multi-echo sequences that inherently rely on magnetic field gradients [17].

The prior commercial embodiments of pMRI known to the inventor herein require a plurality of magnetic gradients and/or gradient reversals. This can generate a large amount of noise, first RF and other electrical noise, and second audible noise. This means that image signal-to-noise ratio is lowered, and that the machine can be extremely loud (up to 120 dB).

This patent specification recognizes and addresses these and other aspects of prior MRI work by providing a new, radically different approach.

SUMMARY OF THE DISCLOSURE

This patent specification describes a new approach using an MRI system to do volume imaging that does not rely for 3D spatial encoding on magnetic gradient switching or additional RF pulses and departs in important ways from the known proposals for hybrid pMRI.

One example of the new approach comprises a gantry with a magnet configured to generate a main magnetic field $B_0$ in an imaging volume, a gradient field generator configured to generate a steady gradient field g in the imaging volume, a radio-frequency (RF) pulse generator configured to apply an excitation RF pulse to the imaging volume, and a multitude of small MR signal receiving coils arranged in a three-dimensional (3D) array surrounding the imaging volume and extending along the $B_0$ field. Each of the receiver coils is configured to simultaneously receive RF energy from the entire imaging volume during MR signal acquisition and output respective MR signals. An MR signal acquisition facility acquires the MR signals and a computer-implemented processor applies image reconstruction algorithms to the MR signals and thereby generates a 3D image of an object in the imaging volume, displayed as such or as two-dimensional (2D) images derived therefrom. The MR signal from each of the coils comprises a time sequence of overall peaks and valleys that can extend over a period of the order of seconds and even minutes in response to the RF pulse, without requiring additional MR signal-encoding RE pulses or MR signal-encoding gradient reversals for spatial encoding or rephasing.

The 3D array of receiving coils comprises M coils along $B_0$ and N coils transverse to $B_0$. Spatial encoding is based on spatial sensitivity parameters of the receiving coils. The gradient field generator is configured to generate the steady gradient field g as a single gradient field maintained throughout the MR signal acquisition, and the acquisition facility is configured to acquire the MR signals in the substantial absence of gradient field reversals or additional RF pulses, although inhomogeneities in the $B_0$ field can be compensated with a few gradient reversals or additional RF pulses. The image reconstruction can involve applying a one-dimensional Fourier Transform or Fourier Series process to the MR signal from the respective coils to generate transformed MR signals, and applying a matrix multiplication process to the transformed MR signals using a matrix related to spatial sensitivities of the receiving coils.

The new approach also comprises carrying out an MRI process comprising applying a main magnetic field $B_0$, a steady gradient magnetic field g, and an excitation radio-frequency (RF) pulse to a three-dimensional (3D) imaging volume, acquiring RF energy for the entire imaging volume with each of a multitude of receiving coils arranged in a 3D array around the imaging volume during MR signal acquisition in the substantial absence of gradient reversals or subsequent RF pulses, applying image reconstruction algorithms to the MR signals to thereby generate a 3D image of an object in the imaging volume, and displaying the 3D image as such or as two-dimensional (2D) images derived therefrom.

An embodiment of another aspect of the new approach is a computer program product embodied in a non-transitory form in a computer-readable medium and comprising instructions that, when executed by a computer system, cause the system to carry out the steps of acquiring magnetic resonance (MR) signals for an entire imaging volume generated from each of a multitude of receiving coils arranged in a 3D array around an imaging volume during MR signal acquisition in the substantial absence of gradient reversals or RF pulses subsequent to an initial RF pulse, applying image reconstruction algorithms to the MR signals to thereby generate a 3D image of an object in the imaging volume, and displaying the 3D image as such or as two-dimensional (2D) images derived therefrom.

BRIEF DESCRIPTION OF THE DRAWING

FIG. 1a illustrates in block diagram form an MRI system according to one embodiment described in this patent specification; FIG. 1b a relevant coordinate system; FIG. 1c illustrates a portion of an array of receiver coils; FIG. 1d illustrates in perspective view a portion of the array of the 3D receiver coils; and FIG. 1e illustrates a stack of 2D arrays of receiver coils.

DETAILED DESCRIPTION OF PREFERRED EMBODIMENTS

Figure 2:
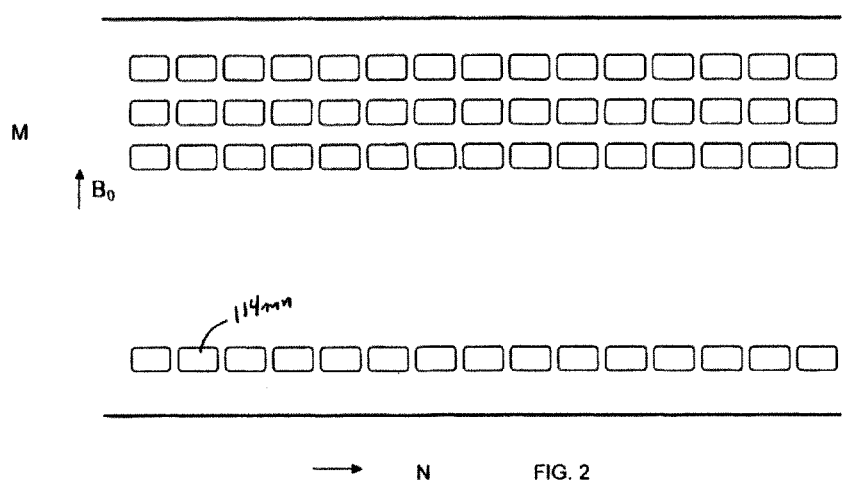
FIG. 2 illustrates an array of receiver coils when unfolded and flattened.

An example of a preferred embodiment can operate by using some of the basic components of a conventional MRI system, such as a magnet generating a main magnetic field $B_0$ in an imaging volume, a source of RF excitation pulses, a source of an a magnetic gradient, a computer configured to process MR signals and to control the overall operation of the system, and a workstation to format and process MR images and allow operator control. The new approach described in this patent specification adds other components, and programs the computer in the system to carry out different operations. The new components include a drastically different 3D array of very small receiver coils surrounding the imaging volume where the output of each of the small coils is an MRI signal comprising contributions from the entire imaging volume. The new approach further includes modifications in the control over, and if desired the structure of, the RF pulse and gradient generators, and providing a different facility for computer-processing the output of the multitude of small receiver coils.

One example of a preferred embodiment is illustrated in block diagram form in FIGS. 1a-1e and comprises an MRI gantry 10 that can be similar to MRI systems currently offered commercially by companies such as Siemens Healthcare and GE Healthcare. For example, gantry 10 comprises a magnet 102 generating a main magnetic field $B_0$, using a superconducting magnet surrounding a cylindrical imaging volume 104, where the main field $B_0$ extends in a z-direction of a Cartesian xyz reference in which the z-direction is along the length of a patient table 110 and the x,y directions are perpendicular to the table length, RF pulse generator 106, steady gradient field generator 108 generating a steady magnetic gradient g, an MR signal acquisition facility 115, and controls over the components and their operation.

Unlike conventional MRI systems, gantry 10 includes a 3D array 112 of a multitude of very small receiver coils (detectors) 114, which array extends both in the direction of the $B_0$ field and in a transverse direction to thereby surround the imaging volume. Also unlike conventional MRI systems, gantry 10 is configured to generate a steady gradient magnetic field g extending, for example, in the x-direction (a $g_x$ field) but does not require gradient field reversals for spatial encoding as in a conventional MRI system although optionally a few gradients or reversals could be used for a different purpose, namely, to compensate for inhomogeneities in the $B_0$ field. Still in addition, gantry 10 differs from conventional MRI systems in that its RF pulse generator is configured to generate a single RF excitation pulse, such as a 90° excitation pulse, but need not generate additional RF pulses during MR signal acquisition for purposes such as spin reversals, except optionally may provide several RF pulses for a different purpose, namely, to compensate for inhomogeneities of the $B_0$ field. For conciseness, this patent specification does not provide details of the conventional MRI components and processes, so as not to obscure the new components and processes that are described in greater detail below.

The 3D array 112 of receiver coils comprises a multitude of very small, loop-shaped receiver coils 114, each for example of the order of several mm along each side. Array 112 can be generally cylindrical in shape, surrounding the imaging volume. The receiver coils 114 are arranged in generally round 2D arrays 116 that can be stacked next to each other in the $B_0$ direction. Each 2D array 116 surrounds the imaging volume. For example, a 3D printing technique can be used to form the conductive elements of each coil (and related conductive lines to the coils) as embedded in a material that is not electrically conductive, such as a polymer, and is tubular or is initially flat but later is rolled into a tubular shape to surround the imaging volume of the MRI scanner. The number of such 2D arrays 116 is related to the desired length of the 3D imaging volume 104 along the $B_0$ direction and the desired spatial resolution in that direction. For example, if the 3D imaging volume 104 is considered as a stack of slices each 1 mm thick in the $B_0$ direction, and if the imaging volume is 20 cm long in the $B_0$ direction, then there can be a stack of approximately 200 2D arrays 116 of receiver coils 114. However, there need not be a one-to-one correspondence between the number of 2D arrays of receiver coils and the number of actual or virtual slices of the imaging volume.

FIG. 2 illustrates an arrangement of small receiver coils 114 when the 3D array 112 of coils is unfolded and flattened for easier visualization. There can be M 2D arrays 116 of coils 114 in the $B_0$ direction, which can but need not correspond to M actual or virtual slices of the imaging volume. Each 2D array 116 can comprise N coils 114, where M×N can be 256×256 in one non-limiting example. M and N are positive integers much greater than unity. Each of the coils 114 is identified by the reference numeral $114_{mn}$, to indicate that it is the m-th coils in the $B_0$ direction, and the n-th coil within the 2D array 116 of coils 114 in a direction transverse to the $B_0$ direction. Each detector 114 is depicted as a single loop. For a spatial resolution of 1 mm and a field of view of 250 mm, each of the loops 114 can be approximately 3 mm perpendicular to $B_0$. Preferably each coil 114 is less than 1 cm in each dimension; more preferably, each is less than 5 mm in each dimension; still more preferably each coil is 3 mm or less in each dimension.

Gantry 10 excites an object in the imaging volume 104 with a single RF pulse, for example a 90° RF pulse, while the object is in the imaging volume and an initial steady gradient field g is being applied to the imaging volume. In the example of a 1.5 T MRI magnet with the $B_0$ field in the z-direction, the initial gradient field can be in the x-direction and can have a typical strength of 45 mT/meter. Unlike in conventional MRI, the initial magnetic field g need not change during MR signal acquisition, and there need not be other gradient fields and reversals thereof for spatial encoding. In addition, there needs to be only an initial RF excitation pulse. The only additional RF pulses and gradients or gradient reversals that can be employed, if desired, serve to compensate for distortions of MR signals from the coils 114 due to inhomogeneities in the magnetic field. This compensation serves to rephase dephasing due to $B_0$ field inhomogeneities but is not required for exciting the object for the purpose of generating MR signals. Thus, the additional RF pulses and gradients/reversals, if any, can be called field inhomogeneity compensating pulses or gradients, or simply compensating RF pulses or gradients.

Figure 3:
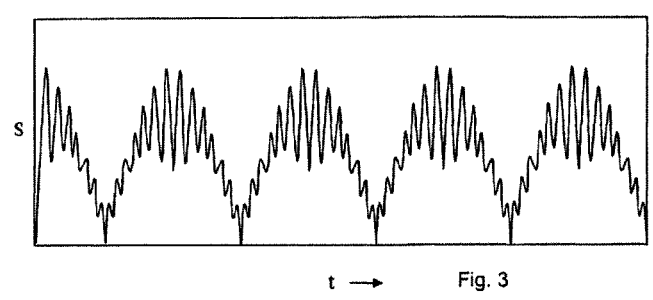
FIG. 3 illustrates an MR signal generated by a receiver coil.

FIG. 3 illustrates an MR signal S that a single receiver coil 20 generates in response to the initial excitation RF pulse. Notably, the response MR signal S does not simply rise and fall, as a conventional MR echo in a conventional MRI system, but rather oscillates, forming repeated overall peaks and valleys without further RF excitation of the imaging volume. This oscillation can go on indefinitely if the T1 and T2 parameters of the object in the imaging volume did not decay in amplitude with time. In practice, the oscillations can provide useful MR signal of the order of seconds and minutes consistent with the quantum decay (spontaneous emission) of the excited state. Even without decay and without gradient switching, the amplitude of the MRI signal S of each of the small coils goes to nominal zero every $\tau=(FOV)/(256\gamma g_x)$ seconds, where FOV is the field of view, $\gamma$ is the gyromagnetic ratio, $g_x$ is the magnetic field gradient in the x direction, and 256 is the image matrix dimension in pixels The new process is explained below in greater detail. As noted, it makes use of a massively parallel, 3D array of very small receiver coils (detectors) 114 arranged around the object being imaged. Unlike the previous proposal for single-slice pMRI (3, 4), each of the small coils 20 in the new approach simultaneously acquires MR signals from the entire 3D imaged volume. This leads not only to markedly reduced imaging times, but also to marked increase in MR signal per unit of time.

While in theory current MRI systems could acquire signal from the entire volume simultaneously by successive application of gradients in the x, y and z directions, and could analyze the signal with a 3D Fourier transform, in practice after each successive gradient in z the entire set of spins would have to be allowed to relax, and then re-excited for further signal acquisition. Otherwise the T2 dephasing would quickly eliminate the signal. Furthermore, the required periods of relaxation would greatly extend actual acquisition times.

In contrast, in the new system described here, which can be identified by the label ULTRA, there is a steady, single gradient g employed throughout the MR signal acquisition. This single magnetic gradient g need not be switched or even varied, and in one preferred embodiment is never switched or varied during MR signal acquisition. As a result, the technique is essentially noise-free both electrically and acoustically. In practice, in order to overcome or reduce the effect of inhomogeneities of $B_0$, the ULTRA process preferably uses a periodic imposition of inhomogeneity-compensating 180° RF pulses, for example approximately every 10 ms. The resulting electrical noise can be a low-frequency hum at approximately 100 Hz.

Figure 4:
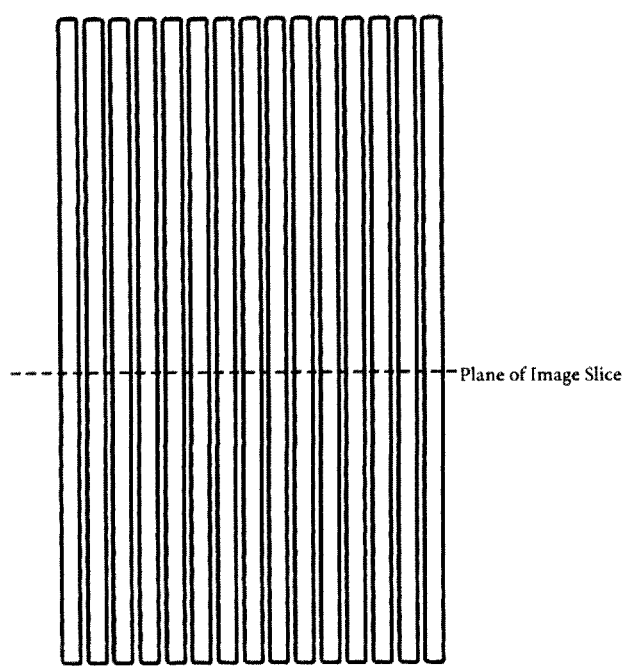
FIG. 4 illustrates a prior art arrangement of receiver coils.

The massively parallel 3D array of small coils (detectors) 114, N×M in number, arranged in a generally cylindrical fashion around the object in the imaging volume, also is very different from the receiver in the earliest description of pMRI [3, 4], where only a single slice would be excited at any given time in order to provide sufficient amplitude of the detected MR signal. 3D image acquisition and 3D image reconstruction were not proposed or contemplated. The detector array that was believed to be most consistent with maximal signal in the earlier pMRI proposals [3,4] consisted of N long parallel loops on a cylinder, arranged in a single layer with long axis parallel to $B_0$, as illustrated in FIG. 4 (where the plane of the imaged slice is perpendicular to the lengths of the coil loops).

In the new ULTRA system it has been unexpectedly discovered that the MR signal per unit time is actually increased, if not maximized, by acquiring MR signals from the entire imaged volume simultaneously, provided the receiver coils (detectors) are made much smaller. The use of such much smaller receiver coils 114 according to the new approach paradoxically enables a much higher rate of acquisition of MR signal.

For simplicity, and to illustrate the new system and method, first consider a hypothetical case in which the parameters T1 and T2 of an object in the imaging volume 104 do not decay with time, so that there is no decay of MR signal with time and the image is defined only by the spin density $\rho_{ijk}$, where (i,j,k) are the quantized (pixelated) coordinates corresponding to (x,y,z) voxels in an object in the imaging volume. The principal steps in an example of the new process can be:
1. Apply a single steady gradient g in a fixed direction, say $g_x$, which remains fixed throughout the MR signal acquisition;
2. Excite all spins in the entire volume of the object being imaged, simultaneously, with a 90 degree RF pulse.

The MR signal $S_{mn;ijk}(t)$ in a small coil (detector) $114_{mn}$ due to volume element (i,j,k) at time (t) in the object in the imaging volume is then $$S_{mn;ijk}(t) = R_{mn;ijk}\rho_{ijk}e^{i\omega t} \quad (2)$$

where $\omega = xg_x$, x is distance in the x-direction, and R is a matrix representing detector spatial sensitivity of coils 114 in 3D array 112, based on a near-field dipole spatial dependence of $1/r^3$, where r is the distance between a given spin and a given small coil (detector) 114, and an angular dependence as given by Maxwell's equations. Such a spatial dependence can be modified at high field strengths and low wavelengths, but this is known in MRI technology and the way to do it is within ordinary skill in that technology.

Since ω is proportional to x, it can simply replace x and Eq. (2) can be rewritten:

$$S^{(\omega)}_{mn;jk}(t) = R^{(\omega)}_{mn;jk}\rho^{(\omega)}_{jk}e^{i\omega t} \quad (3)$$

where the left hand side is the amplitude of the MR signal in small coil (detector) $114_{m,n}$ due to the volume element at location (j,k) in the yz plane defined by frequency ω (or, in other words, the yz plane defined by fixed x). Then:

$$S^{(\omega)}_{mn}(t) = \sum_{j,k} R^{(\omega)}_{mn;jk}\rho^{(\omega)}_{jk}e^{i\omega t} \quad (4)$$

Let the one dimensional Fourier transform of S(t) be $\mathcal{S}^{(\omega)}$, where $\mathcal{S}^{(\omega)}$ is a matrix representing the $\omega^{th}$ component of the set of Fourier transformed MR signals in all small coils 114 (all detectors).

With this definition, Eq. (4) can be rewritten as:

$$\rho^{(\omega)} = \{R^{(\omega)}\}^{-1}\mathcal{S}^{(\omega)} \quad (5)$$

which in words means the following: the two-dimensional matrix representing the spin densities within the plane defined by frequency ω, is the product of the inverse spatial sensitivity matrix of the small coils 114 in 3D array 112 and the matrix representing the Fourier transform of the time dependent signals in all small coils (detectors) 114.

Eq. (5) above has some similarities to Eq. (15) of reference [4] but explains a process that is not described or suggested in reference [4]. The left hand side of Eq. (5) above represents a two-dimensional image plane in a process based on a 3-dimensional structure where all image planes are acquired simultaneously. In contrast, the left hand side of Eq. (15) of reference [4] represents a line of image data in the context of a 2-dimensional structure where all lines in only a single image plane are acquired simultaneously. Thus, Eq. (5) above achieves the results described in this patent specification in the context of the radically different structure of a 3D array 112 of receiver coils 114 each of which is made much smaller than in reference [4], and the entire imaging volume can now be imaged with one excitation.

Eq. (5) above embodies a key concept of the new approach and demonstrates that the entire imaging volume, including all planes of equal frequency defined by a single linear and steady gradient g, can be decoded uniquely by first performing a Fourier transform of the MR signal in each small detector 114, and then multiplying the transformed signals by an inverse of the matrix of spatial sensitivities of the receiver coils 114. It can now be seen that each small detector loop 114 receives MR signal information from the entire imaging volume. Therefore all of the MR signals from all of the spins, all of the time, are detected by each receiver coil 114 in the entire set of N×M detectors 114. This vastly increases the rate of signal acquisition and puts ULTRA in a unique category, since in known conventional embodiments of MRI at any given time only a partial volume of spins gives rise to MR signals. It therefore follows that ULTRA is not only faster than known previous proposals and embodiments but also gives rise to much greater rates of MR signal acquisition. Put another way, if the entire set of N×M detectors 114 in ULTRA were joined to form one large conventional detector, this would capture a much greater MR signal than a large conventional detector employing gradient reversals, since all spins in the object volume would be contributing to the signal at all times. Nevertheless such an arrangement would not make instant 3-dimensional imaging possible, because there is only one coil. ULTRA takes advantage of an inherently very high signal by distributing it throughout a very large number of small coils, and then reconstructing it. With reference to FIG. 2, where the matrix of receiver coils 20 is mapped on a two-dimensional plane, it now becomes apparent that ULTRA can be considered a holographic technique. That is, the entire three dimensional volume of spin density in the imaging volume can be simultaneously and uniquely encoded in a two dimensional plane (in which the generally cylindrical array of small coils can be unfolded).

The MR signal processing described above can be carried out in a processor such as currently used in commercial MRI systems but programmed differently to carry out the processing, using a program that a person of ordinary skill in MRI and computer programming can write without undue experimentation based on the explanation herein. Such a program can become a computer program product when stored in a non-transitory manner in computer-readable media such an optical disc, a thumb drive, or a hard disc.

Referring again to FIG. 3, as noted above the oscillating MR signal would go on forever for infinite T1 and T2, or in practice until the quantum decay (spontaneous emission) of the excited state, which can be on the order of many seconds and even minutes. The signal is periodic, and even without decay, and even without gradient switching, its amplitude (vertical axis in FIG. 3) would go to nominal zero every $\tau=(FOV)/(256\gamma g_x)$ seconds, where FOV is the field of view, $\gamma$ is the gyromagnetic ratio, $g_x$ is the magnetic field gradient in the x direction, and 256 is the image matrix dimension. Therefore, in the special, hypothetical case of infinite T1 and T2, the signal is a periodic function such that within each period $\tau$ the amplitude would go to nominal zero at least once, as dictated by $g_x$. In reality, not only are T1 and T2 finite, but for short time scales the MR signal will decay because of inhomogeneities in $B_0$. A rough estimate of the latter decay time can be made by assuming an inhomogeneity of p parts per million. In the example of a 1.5 T (Tesla) MRI system, where the frequency is 65 MHz, and for p=1, the signal would begin to decay in a significant way after $\frac{1}{65}$ seconds, or approximately 15 ms. In order to correct for this, a periodic inhomogeneity-compensating 180° RF pulse can be applied, say every 10 ms. For p=2, the RF pulse would have to be applied approximately every 5 ms, etc. The imposition of such inhomogeneity-compensating RF pulses would lead to a low-frequency humming sound, which would be quite different from the high frequency, high decibel sounds of gradient reversals which characterize current MRI technology. Note that these inhomogeneity-compensating RF pulses are not used to encode, only to re-phase any dephasing caused by inhomogeneity in $B_0$.

While the foregoing description pertains to spin density images, in clinical MRI embodiments images can be of interest that are sensitive also to the spin-lattice relaxation time, T1, and the spin-spin relaxation time, T2. Such images also can be obtained using the ULTRA principles explained in this patent specification. Note first that from each broad peak in FIG. 3 an entire 3-dimensional image can be created. If T1 and T2 were infinite, then each broad peak would have the same height (MR signal amplitude). For 10 peaks at a time, comprising say 10 ms of MR signal, the entire signal can be averaged into one image having high signal-to-noise ratio. The next set of images, from 10-20 ms, can likewise be averaged into one image, and so on, until signal has been acquired for, say, 10 high-signal image sets spanning 100 ms. T2 can then be determined for each pixel within the imaging volume by fitting it to an exponential decay generated from all image sets.

Likewise, after 100 ms the spins can be rephased by a partial excitation RF pulse, and the process repeated, giving yet more MR signal for the T2-weighted images, while at the same time allowing for an estimation of T1, by the relative amplitudes of the broad peaks compared with the amplitudes after the initial 90° RF excitation pulse. The entire process can be repeated every 100 ms, so that after, say, 1000 ms all information pertaining to both T1 and T2 can be obtained with high signal-to-noise ratio. Still likewise, similar principles can be used to create inversion-recovery images or diffusion-weighted images. For example, inversion-recovery images can be made modifying the conventional 180° RF pulse, followed after a time T1 by a 90° RF pulse, so that the 90° pulse occurs, say, at time TI−50τ, with acquisition beginning at that time, and continuing until TI+50τ. Diffusion-weighted images might be obtained in analogy with conventional imaging, by applying diffusion gradients every few milliseconds.

While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

The foregoing has been described in some detail for purposes of clarity, but it will be apparent that certain changes and modifications may be made without departing from the principles thereof. It should be noted that there are alternative ways of implementing both the processes and apparatuses described herein. For example, the disclosed process is intended to work by using an MR signal acquisition that does not include any gradient reversals or MR signal-encoding RF pulses after the initial RF excitation pulse. However, a substantial absence of such gradient reversals or subsequent RF pulses may be sufficient, where "substantial absence" for the purpose of this patent specification includes the use of some gradient reversals and subsequent signal-encoding RF pulses that still allow the reconstruction of clinically useful 3D images from MR signals that are due to the initial RF excitation pulse and the initial gradient that remains steady throughout image acquisition. Accordingly, the present embodiments are to be considered as illustrative and not restrictive, and the body of work described herein is not to be limited to the details given herein, which may be modified within the scope and equivalents of the appended claims.

CITED REFERENCES (INCORPORATED BY REFERENCE)

1. Lauterbur P C, Image formation by induced local interactions. Nature 1973; 242(1): 190.

2. Mansfield P, Pykett I L, Biological and medical imaging by NMR. J. Mag. Res. 1983; 29(2):355-373.
3. Hutchinson M, Raff U, Subsecond Data Acquisition Using Multiple Detectors. Proceedings, Society for Magnetic Resonance in Medicine, 6th Annual Meeting, New York. 1987; Supplement S1: 459.
4. Hutchinson M, Raff U, Fast MRI Data Acquisition Using Multiple Detectors. Mag. Res. Med. 1988: 6:87-91.
5. Kelton J R, Magin R L and Wright S M, An algorithm for rapid image acquisition using multiple receiver coils. Proceedings of the SMRM 8th Annual Meeting (1989) p. 1172.
6. Ra J B, Rim C Y. Fast imaging using subencoding data sets for multiple detectors. 1993; Mag. Res. Med. 30(1): 142-145.
7. Roemer P B, Edelstein W A, Hayes C E, Souza S P, Mueller O M, The NMR phased array. Mag. Res. Med. 1990; 16:192-225.
8. Ocali O, Atalar E, Ultimate Intrinsic Signal-to-Noise Ratio in MRI. Mag. Res. Med. 1998; 39:462-473.
9. Sodickson D K, Manning W J, Simultaneous acquisition of spatial harmonics (SMASH): Fast imaging with radiofrequency coils. Mag. Res. Med. 1997; 38(4):591-603.
10. Pruessman K P, Weiger M, Scheidegger M B, Boesiger P, SENSE: Sensitivity encoding for fast MRI. Mag. Res. Med. 1999; 42(15):952-962.
11. Ohliger M A, Grant A K, Sodickson D K, Ultimate intrinsic signal-to-noise ratio for parallel MRI: Electromagnetic field considerations. 2003. Mag. Res. Med. 2003; 50:1018-1030.
12. Wiesiger F, Boesiger P, Pruessman K, Electrodynamics and ultimate SNR in parallel MR imaging. Mag. Res. Med. 2004; 52:376-390.
13. Keil B, Wald L L, Massively parallel MRI detector arrays. J. Mag. Res. 2013; 229:75-89.
14. McDougall M P, Wright S M, 64 channel array coil for single echo acquisition. Mag. Res. Med. 2005; 54:386-392.
15. Halpern-Manners N W, Kennedy D J, Trease D R, Teisseyre T Z, Malecek N S, Pines A, Bajaj V S, Gradient-free microfluidic flow labeling using thin magnetic films and remotely detected MRI, J. Mag. Res. 2459 (2014) 135-140.
16. Sharp J C, King S B, MRI Using Radiofrequency Magnetic Field Phase Gradients, Mag. Res. Med. 63:151-161 (2010).
17. Yepes-Calderon F, Velasquez A, Lepore N, Beuf O, Magnetic Resonance Image Enhancement by Reducing Receptors' Effective Size and Enabling Multiple Channel Acquisition, 978-1-4244-7929-0/14 2014 IEEE (2014) 2420-2423.
18. Hutchinson M, Raff U, Is the Fastest MRI a Hologram?, J Neuroimaging 2014; 24; 537-542 (Vol 24 No 6 November/December 2014)

The invention claimed is:

1. A magnetic resonance imaging (MRI) system configured to simultaneously acquire MR signals from an entire imaging volume using spatial sensitivity parameters of a multitude of small receiver coils without a need for spatial encoding by plural gradient reversals or RF pulses in addition to an initial excitation RF pulse, comprising:
a gantry including a magnet configured to generate a main magnetic field $B_0$ in an imaging volume, a gradient field generator configured to generate a steady gradient field g in the imaging volume, and a radio-frequency (RF) pulse generator configured to apply said initial excitation RF pulse to the imaging volume;
a multitude of MR signal receiving coils arranged in a three-dimensional (3D) array surrounding the imaging volume and extending along the $B_0$ field and transversely to the $B_0$ field;
each of the receiver coils being configured to simultaneously receive RF energy from the entire imaging volume during MR signal acquisition and output respective MR signals;
an MR signal acquisition facility configured to acquire the MR signals absent spatial encoding by plural gradient reversals or additional RF pulses;
a computer-implemented processor configured to apply image reconstruction algorithms to the MR signals and thereby generate a 3D image of an object in the imaging volume; and
a display facility configured to display the 3D image as such or as two-dimensional (2D) images derived therefrom.

2. The MRI system of claim 1 in which the MR signal from each of the coils comprises a time sequence of overall peaks and valleys that extends over a period of the order of at least seconds in response to the initial RF pulse and without requiring additional RF pulses or gradient reversals for spatial encoding.

3. The MRI system of claim 1 in which the 3D array of receiving coils comprises M coils along $B_0$ and N coils in each of a multitude of adjacent planes each transverse to $B_0$.

4. The MRI system of claim 1 in which the RF pulse generator is further configured to generate magnetic field inhomogeneity-compensating RF pulses after the initial RF pulse.

5. The MRI system of claim 1 in which the gradient field generator is configured to maintain the steady gradient field g throughout the MR signal acquisition.

6. The MRI system of claim 1 wherein the acquisition facility is configured to acquire the MR signals in the substantial absence of gradient field reversals.

7. The MRI system of claim 1 wherein the acquisition facility is configured to acquire the MR signals in the substantial absence of RF pulses subsequent to the initial RF excitation pulse.

8. The MRI system of claim 1 in which the processor is configured to apply a Fourier Transform or Fourier Series process to the MR signals to generate transformed MR signals, and to apply a matrix multiplication process to the transformed MR signals using a matrix related to spatial sensitivities of the receiving coils.

9. The MRI system of claim 1 in which the MR signals from each of the coils conform to a succession of overall peaks and one or both of the acquisition facility and the processor is configured to combine the MR signals of successive multi-peak sets of the overall peaks and the processor is configured to derive an estimate of at least one of T1 and T2 by comparing the successive sets of combined signals.

10. The MRI system of claim 9 in which the RF pulse generator is configured to generate a partial excitation RF pulse rephrasing spins at a time during the acquisition and combining of MR signals, and the processor is configured to derive an estimate of T1 by comparing combined signals obtained before and after the rephrasing RF pulse.

11. The MRI system of claim 1 in which RF generator is further configured to generate and inversion-recovery RF pulse and the processor is further configured to process the MR signals into an inversion-recovery image.

12. The MRI system of claim 1 in which the gradient field generator is configured to apply a diffusion-gradient and the processor is configured to process the MR signals into a diffusion-weighted image.

13. A magnetic resonance imaging (MRI) method comprising:
applying a main magnetic field $B_0$, a gradient magnetic field g, and an initial excitation radio-frequency (RF) pulse to a three-dimensional (3D) imaging volume;
acquiring MR signals for the entire imaging volume from each of a multitude of receiving coils arranged in a 3D array around the imaging volume, during MR signal acquisition in the substantial absence of spatial-encoding gradient reversals or RF pulses subsequent to the initial excitation RF pulse;
applying computer-implemented image reconstruction algorithms to the MR signals to thereby generate a 3D image of an object in the imaging volume; and
displaying the 3D image as such or as two-dimensional (2D) images derived therefrom.

14. The method of claim 13 in which the gradient magnetic field g is a single field maintained throughout the MR signal acquisition.

15. The method of claim 13 including applying, during MR signal acquisition, at least one of inhomogeneity-compensating gradient reversals and inhomogeneity-compensating subsequent RF pulses to compensate for inhomogeneities in the $B_0$ field.

16. The method of claim 13 including applying, during the MR signal acquisition, both inhomogeneity-compensating gradient reversals and inhomogeneity-compensating subsequent RF pulses to compensate for inhomogeneities in the $B_0$ field.

17. The method of claim 13 in which the applying of the image reconstruction algorithm further includes obtaining estimates of at least one of T1 and T2.

18. The method of claim 13 in which the applying of the image reconstruction algorithm further includes obtaining an inversion-recovery image.

19. The method of claim 13 in which the applying of the image reconstruction algorithm further includes obtaining a diffusion-weighted image.

20. A magnetic resonance imaging (MRI) method comprising:
acquiring MR signals from an object in an imaging field in response to an initial RF excitation of the object but in the absence of subsequent spatial encoding RF excitation pulses and spatial encoding gradient magnetic field reversals; and
reconstructing a three-dimensional (3D) image of the object from the MR signals.

21. The method of claim 20 in which the acquiring comprises spatial encoding using spatial sensitivities of receiving coils.

22. The method of claim 20 in which the acquiring of MR signals comprises acquiring the signals in the presence of a single magnetic gradient that remain unchanged throughout signal acquisition.

23. The method of claim 20 in which the signal acquisition comprises acquiring from each of plural coils a succession of overall peaks of the MR signal, and wherein the reconstructing comprises reconstructing a 3D image of the object from a set of a single peak from each of the coils.

24. The method of claim 20 including applying at least one of inhomogeneity-compensating gradient reversals and inhomogeneity-compensating RF pulses to compensate for inhomogeneities in a main magnetic field $B_0$ applied to the object.

25. A computer program product embodied in a non-transitory form in a computer-readable medium and comprising algorithms that, when executed by a computer system, cause the system to carry out the steps of:
acquiring magnetic resonance (MR) signals for an entire imaging volume generated from each of a multitude of receiving coils arranged in a 3D array around an imaging volume, during MR signal acquisition in the substantial absence of spatial encoding gradient reversals or spatial encoding RF pulses subsequent to an initial, encoding RF pulse;
applying image reconstruction algorithms to the MR signals to thereby generate a 3D image of an object in the imaging volume; and
displaying the 3D image as such or as two-dimensional (2D) images derived therefrom.

* * * * *